United States Patent
Hahn et al.

(10) Patent No.: US 7,172,866 B2
(45) Date of Patent: Feb. 6, 2007

(54) METHODS AND GEL COMPOSITIONS FOR ENCAPSULATING LIVING CELLS AND ORGANIC MOLECULES

(75) Inventors: Soonkap Hahn, San Diego, CA (US); Roberto Fagnani, Solana Beach, CA (US); Xiaofan Dong, San Diego, CA (US); Carl F. Edman, San Diego, CA (US); Pavel Tsinberg, San Diego, CA (US)

(73) Assignee: Biocept, Inc., Carlsbad, CA (US)

( * ) Notice: Subject to any disclaimer, the term of this patent is extended or adjusted under 35 U.S.C. 154(b) by 483 days.

(21) Appl. No.: 10/398,725

(22) PCT Filed: Apr. 2, 2002

(86) PCT No.: PCT/US02/10411

§ 371 (c)(1),
(2), (4) Date: Apr. 8, 2003

(87) PCT Pub. No.: WO02/081662

PCT Pub. Date: Oct. 17, 2002

(65) Prior Publication Data

US 2004/0029241 A1 Feb. 12, 2004

Related U.S. Application Data

(60) Provisional application No. 60/281,268, filed on Apr. 3, 2001.

(51) Int. Cl.
*C12N 5/00* (2006.01)
(52) U.S. Cl. .......................... 435/6; 435/7.1; 435/325; 435/395; 435/287.2; 527/301; 527/204; 436/518
(58) Field of Classification Search .................. 435/6, 435/7.1, 325, 395, 287.2; 527/301, 204; 436/518
See application file for complete search history.

(56) References Cited

U.S. PATENT DOCUMENTS

| | | |
|---|---|---|
| 4,794,090 A | 12/1988 | Parham |
| 5,175,229 A | 12/1992 | Braatz |
| 5,403,750 A | 4/1995 | Braatz |
| 5,573,934 A | 11/1996 | Hubbell et al. ............. 435/177 |
| 5,849,368 A | 12/1998 | Hostettler et al. .......... 427/536 |
| 5,962,280 A | 10/1999 | Mukouyama et al. ....... 435/109 |
| 6,174,683 B1 * | 1/2001 | Hahn et al. .................... 435/6 |
| 6,433,134 B1 | 8/2002 | Patron et al. ................ 530/300 |
| 6,642,046 B1 * | 11/2003 | McGarry et al. ......... 435/287.2 |
| 6,818,018 B1 * | 11/2004 | Sawhney ................. 623/11.11 |

2003/0134294 A1 * 7/2003 Sandford et al. .............. 435/6

FOREIGN PATENT DOCUMENTS

EP   1 025 860 A   8/2000

* cited by examiner

*Primary Examiner*—Leon B Lankford, Jr.
(74) *Attorney, Agent, or Firm*—Fitch, Even, Tabin & Flannery

(57) ABSTRACT

A method for encapsulating biologics within a hydrogel by using an aqueous solution of an isocyanate-functional hydrogel prepolymer which is mixed with an amount of biologics and an aqueous solution containing a dithiol crosslinking agent under physiological pH conditions. An additional bidentate crosslinking agent may be included. The product of such method may be a bioreactor or an assay device having a plurality or different biologics encapsulated at predetermined locations in a substrate.

X = Polyethyleneoxide or copolymer of polyethyleneoxide and polypropyleneoxide capped with polyisocyanates and lightly crosslinked with polyols
Y = Polyethyleneoxide or copolymer of polyethyleneoxide and polypropyleneoxide
Z = Polymer or monomer
W = Nuclephile such as amine, hydroxyl or like Crosslinking between prepolymers (I and I or I and II) until all isocyanates are consumed.

11 Claims, 2 Drawing Sheets

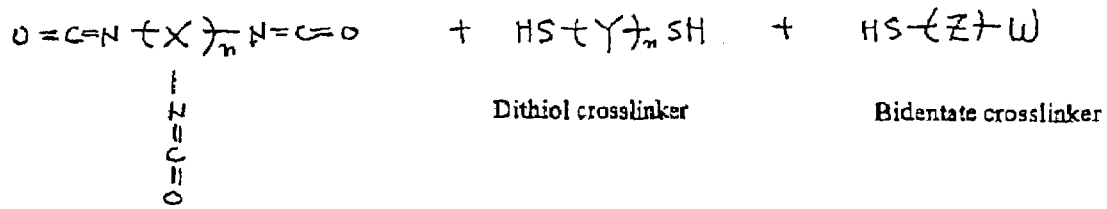

X = Polyethyleneoxide or copolymer of polyethyleneoxide and polypropyleneoxide capped with polyisocyanates and lightly crosslinked with polyols Dithiol crosslinker Y = Polyethyleneoxide or copolymer of polyethyleneoxide and polypropyleneoxide Bidentate crosslinker Z = Polymer or monomer
W = Nucleophile such as amine, hydroxyl or like

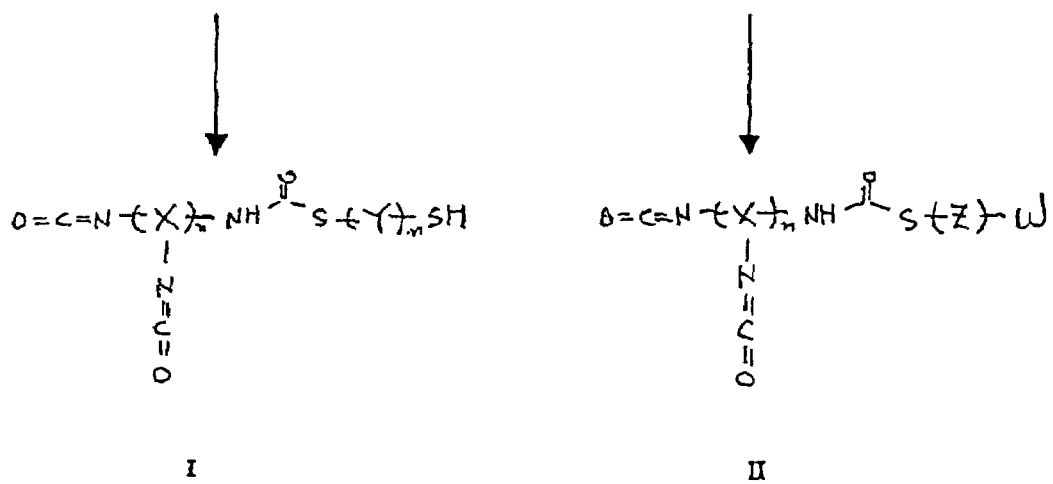

I  II

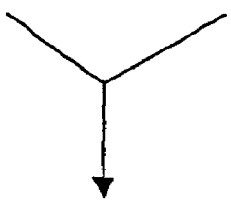

Crosslinking between prepolymers (I and I or I and II) until all isocyanates are consumed.

FIG 2.

METHODS AND GEL COMPOSITIONS FOR ENCAPSULATING LIVING CELLS AND ORGANIC MOLECULES

This application is a 371 of PCT/US02/10411 filed Apr. 2, 2002 which claims priority from U.S. Provisional Patent Application Ser. No. 60/281,268, filed Apr. 3, 2001, the disclosure of which is incorporated herein by reference.

FIELD OF THE INVENTION

The present invention relates to systems and methods for forming polyurethane hydrogels useful for encapsulating biologics, such as living cells, proteins, enzymes, antibodies and small organic molecules, and to the compositions which result therefrom. More specifically, the present invention relates to the formulation and use of a polymerization process employing biocompatible polymers and biocompatible polymerization conditions, such as neutral pH, where there is maintenance of an aqueous environment and preservation of physiologically relevant osmolarity throughout the polymerization process, as well as to bioassays utilizing such improved resultant products. This invention represents a significant development in the art of encapsulation of certain materials and a significant advancement, from certain standpoints, of the process described in U.S. Pat. No. 6,174,683, which is assigned to the assignee of this application.

DESCRIPTION OF PRIOR ART

The use of enzymes, antibodies, peptides, or other bioactive molecules, e.g. aptamers, has received increasing attention as tools for screening in the fields of bioassays and proteomics. As part of this development, the use of hydrogel supports for these bioactive materials has also gained in importance. Hydrogels are defined as water-containing polymeric matrices. In particular, hydrogels provide a support for biomaterials that more closely resembles the native, aqueous, cellular environment, as opposed to a more denaturing environment that results when proteins or other materials are directly attached to a solid support surface using other molecular scale linkages, such as coatings.

Certain hydrogels have previously been described as matrix supports for biomolecules and/or living cells, and these include alginates, alginates modified to permit crosslinking, acrylamide-based hydrogels, and polyethylene oxide-based hydrogels. In general, however, there is frequently difficulty in reconciling the gel polymerization and encapsulation requirements with the gentle conditions requisite for maintaining the viability or activity of live cells or certain active proteins. In addition, many of the materials suitable for these gentle conditions, e.g. alginate-based polymers, lack the structural requirements and/or biostability necessary for broad applications.

Alginate gels have been widely utilized for immobilization of eukaryotic cells and proteins. This form of hydrogel is generally benign and biocompatible during the encapsulation process; however, it can suffer from a lack of structural stability. Alginates are thus sometimes combined with multivalent cations to form more stable, ionically cross-linked gels. However, upon exposure to physiologically relevant buffers and environments, divalent cations tend to exchange with monovalent species, and the polymer often loses structural integrity. As a result, alginates are somewhat undesirable hydrogels for encapsulating biomolecules and living cells. Moreover, the overall manufacturability of alginate gels is difficult, further lessening the desirability and applicability of such a gel system.

Polyacrylamide hydrogel systems have also received considerable attention as matrices for attaching biomolecules and encapsulation vehicles. For example, Arenkov, et al. (*Anal. Biochem.* 278, 123–131 (2000)), describe gel pad arrays formed by photoinitiated polymerization of acrylamide/bisacrylamide mixtures using methylene blue as the photocatalyst. Proteins are then covalently linked to each gel pad following application to the micromatrix either by crosslinking with glutaraldehyde or by chemical modification of carbohydrate moieties present on select proteins to allow subsequent chemical linkage to the gel support. However, such a method of linkage can be potentially very damaging to the integrity and/or activity of the protein, and it may also require the presence of sugar residues not ubiquitously found on all proteins.

Alternative to the use of polyacrylamide-based hydrogels are the use of those composed primarily of polyethylene oxide (PEO) polymerization units. These polymers can offer a number of distinct advantages in the areas of biocompatibility, diffusion of small molecules and manufacturing process control. For example, the grafting of PEO onto serum albumin significantly reduces immunogencity of the native albumin (Abuchowski, et al. 1977). Hubbell, et al. (U.S. Pat. No. 5,573,934 and related patents) teach the use of polyethylene glycol polymers for encapsulating cells using a dye-based photoinitiated free radical-based polymerization process.

In the aforementioned polyacrylamide or PEG polymeric gels, initiation of polymerization requires the addition of a separate, photoactivatable catalyst and/or the addition of free radical-generating polymerization accelerators, separate and distinct from the polymer components or subunits. Chudzik and Anderson (U.S. Pat. No. 6,156,345) teach the use of polymer initiator groups which are pendant from the polymerizable groups and thus avoid the separate addition of initiator components.

Mixed polymer/alginate systems have also been devised to overcome limitations inherent in each system alone. For instance, Desai, et al. (U.S. Pat. No. 5,334,640) employ mixtures of an ionically cross-linked biocompatible component with a covalently linked component. However, the overall process remains dependent upon photoinitiated, free radical-based polymerization.

Use of methodologies incorporating free radicals as essential elements within such a process is a generally undesirable feature of many of the encapsulation/polymerization techniques in present use. For example, in cell encapsulation with acrylamide gels, "polymerization of acrylamide generates heat and free radicals, causing loss of in the chemiosmotic integrity and enzymatic activity of the immobilized cells" (see Poncelet De Smet, et al. in "Fundamentals of Animal Cell Encapsulation and Immobilization", Mattheus F. A. Goosen, editor, CRC Press, Boca Raton, Fla., 1993, p. 301). It is therefore desirable to provide a polymerization process which does not use free radicals to initiate polymerization, thereby avoiding potential harm to encapsulated cells and biomolecules. It is also desirable to utilize polymers which have both structural and mechanical durability in biological situations and uses, particularly ones which are truly biocompatible, i.e. non-toxic to the encapsulated biomolecule or cell and to the surrounding media or host.

Wood, et al. teach the use of various cross-linking polymer systems, including a polyurethane-based hydrogel formed from isocyanate-functional prepolymers, to form a cross-linked polymer to encapsulate microbial cells (U.S. Pat. Nos. 4,436,813 and 4,732,851). Also described are methods using polyazetidine prepolymers and carboxymethylcellulose which can be crosslinked with polyvalent ions. Direct contact of isocyanates with the microbial cells which occurs in the encapsulation within such a polyurethane-based hydrogel and exposure to other potentially toxic conditions may not be suitable for the encapsulation of certain sensitive biological materials.

In the '683 patent, a polyurethane-based hydrogel prepolymer is used to simultaneously derivatize biomolecules, such as nucleic acid probes, within its structure during polymerization. Such a polymerization process can use PEG-based prepolymers and is advantageous from its avoidance of free radicals or other agents as a result of its employ of water to initiate polymerization. However, because organic solvents are often employed in the prepolymer formation, derivitization and/or solubilization, the process may still be toxic to certain sensitive biological materials, such as living mammalian cells.

In brief, there remains a particular need for truly benign, non-toxic, biocompatible and mechanically robust hydrogel polymers and associated polymerization methodology in order to encapsulate certain biologics, such as sensitive proteins, enzymes, antibodies and living cells, in a useful and economically feasible fashion, which can provide products that are well suited for assays and other applications.

SUMMARY OF THE INVENTION

It is an object of the invention to provide a method for biocompatible polymerization of isocyanate-modified biocompatible macromers to either directly or indirectly encapsulate or coat biologics, i.e. living cells, proteins, nucleic acids and other bioactive materials and compounds, including small organic molecules. The polymerization process is truly biocompatible as it employs no organic solvents. This novel process utilizes thiol-based crosslinkers which reduces the crosslinking of biomaterials within the hydrogel, thereby rendering the process capable of encapsulating and attaching such biological material in forms particularly suitable for diagnostic and therapeutic use, for example, microarrays of proteins or cells or other organic compounds for high-throughput testing.

The method of polymerization employs thiol-containing crosslinkers and selective reaction conditions, specifically neutral pH and aqueous buffers, to preferentially favor the reaction of sulfhydryl groups, as opposed to amines, as the preferred conjugation nucleophile where water is present during polymerization; this provides mild, non-radical reaction conditions that allow gentle encapsulation which is of particular importance to biomolecules and living cells. The porosity of the encapsulating polymer can be advantageously varied, and the encapsulation process permits deposition, onto glass slides or other surfaces, of discrete hydrogel droplets in spots or layers that encapsulate cells, proteins or other organic molecules, either directly or indirectly through binding agents, or alternatively by forming droplets or spheres that separately encapsulate such biologics. Moreover, the overall encapsulation/polymerization process comprises fewer steps than comparable methodologies, thereby simplifying and easing process development. Because the resultant polymers can provide antibody or enzymatic arrays and viable cell encapsulation, the potential employment of such materials in bioreactors, biosensors, biochips and artificial organs is facilitated. Such encapsulated cells are expected to serve as a logical extension of bioassay development for complex biopathway screening, and encapsulated cells will be useful tools in bioreactors for economically generating complex therapeutic agents and materials. In addition, encapsulated living cells may potentially serve as artificial organs or biosensors, responding as needed to altered or toxic environments. Microarrays of encapsulated cells or other such biologics are also expected to be useful in high throughput biological testing.

BRIEF DESCRIPTION OF THE DRAWINGS

FIG. 2 is a diagrammatic view, similar to FIG. 1, of an alternative crosslinking reaction embodying various features of the present invention.

DETAILED DESCRIPTION OF THE PREFERRED EMBODIMENTS

Figure 1:
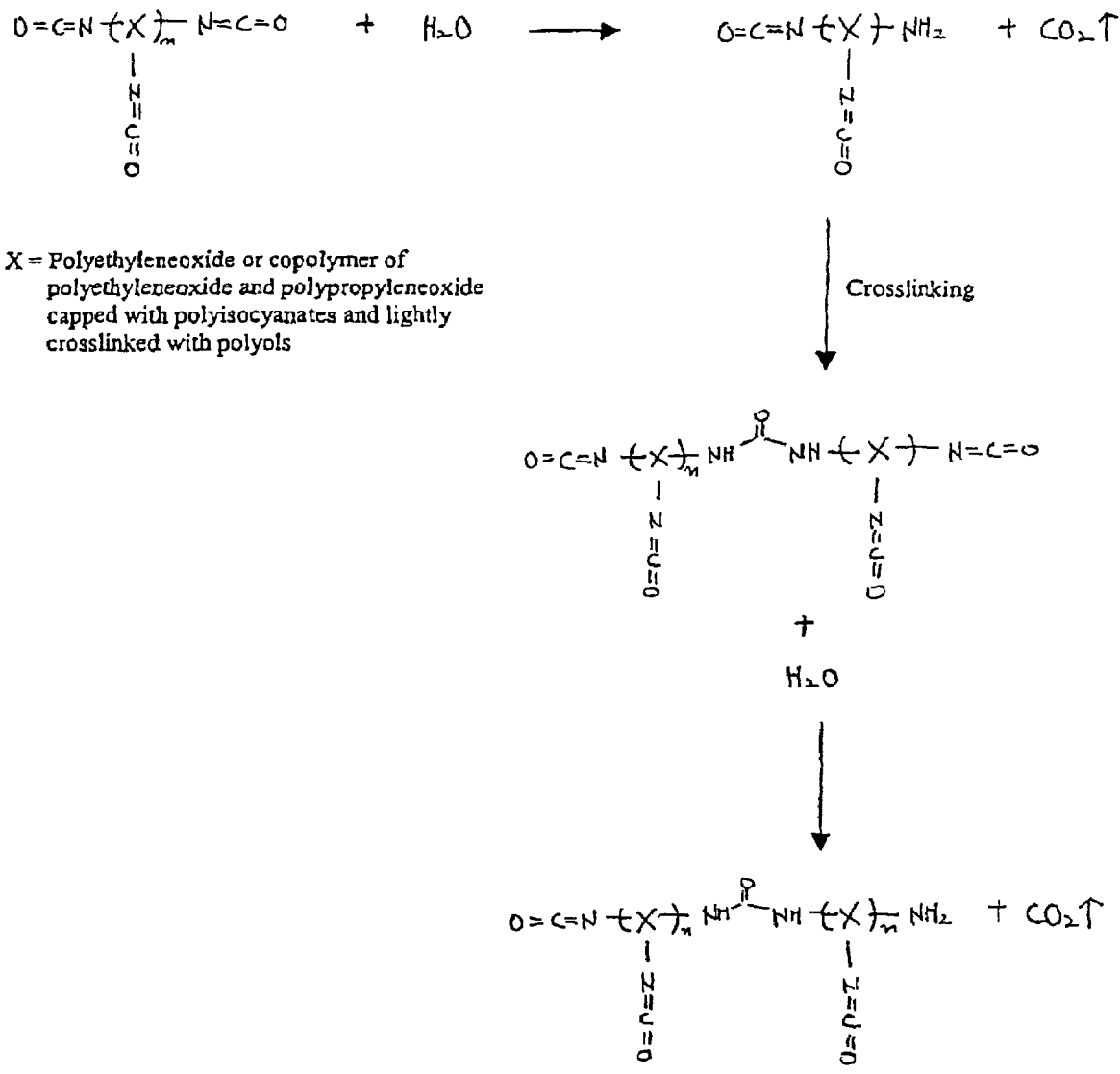
FIG. 1 is a diagrammatic view showing a mechanism of cross-linking prepolymers.

Water is often added to cure or initiate the crosslinking of isocyanate-functional prepolymers. This is in contrast to processes employing free radical-based methodology, e.g. UV-induced photopolymerization, that is used to generate reactive species suitable for forming covalent linkages between prepolymer units. Isocyanate-functional groups are covalently linked to a prepolymer of choice, and such addition of water produces an active primary amine at a certain frequency by conversion of some isocyanate moieties, based upon temperature and pH. Such primary amines subsequently react with other isocyanates attached to other prepolymer units, thereby covalently linking the prepolymer units together, as illustrated in FIG. 1; this is generally representative of certain reactions utilized in the '683 patent. This process leads to the generation of an optically transparent, urea-based hydrogel, so long as reactivity of the prepolymer and reaction conditions are controlled to prevent gas bubble formation and/or precipitation of the polymer. During such a polymerization process, various biological entities or small molecules, i.e. biologics, can be present or can be added to create biologically active hydrogels. The term biologics, for purposes of this patent application, should be understood to include living cells, proteins, such as antibodies, other bioactive materials, both natural or synthetic, and small organic molecules which function bioactively. It can thus be seen that the size of a biologic may vary substantially and, as explained hereinafter, molecules of small size may desirably be provided with anchoring moieties.

The '683 patent describes the addition of primary amine-derivatized oligonucleotides to isocyanate-functional prepolymers in order to produce oligonucleotide arrays that are attached to a solid support surface. An advantageous feature of such a process is that, during the completion of the polymerization reaction between isocyanate prepolymer units, the oligonucleotides will become covalently linked to the polymer matrix. However, such a method, based upon amine conjugation, may not be suitable for certain sensitive biologics, e.g. certain proteins and living cells. Because primary amines are components of all proteins including those present on the surface of living cells, e.g. ligand receptor proteins, ion channel proteins and cell-to-cell adhesion proteins, extensive derivatization or conjugation of such amines directly to the isocyanate-functional prepolymer may lead to the protein's inactivation, denaturation or altered functionality. It has now been found that this possibility is minimized as a result of employing a new crosslinking approach that relies primarily upon thiol groups, instead of amines, for this purpose.

Thiol-based crosslinking agents serve as mediators of the cross-linking reaction between isocyanate groups on different prepolymers, as opposed to employing amine functionalities. Of course, in an aqueous environment, a certain percentage of the isocyanate groups will undergo hydrolysis; however, the primary amines formed as a result will have pKa values in the range of 9 to 10. By maintaining a neutral pH, the vast majority of these amines will be protonated and therefore will not participate in the polymerization process. As a neutral pH, 6.5 to 7.5 is preferred, 6.6 to 7.1 is more preferred and approximately pH 7.0 is most preferred. The presence of such thiol-containing species will cross-link unreacted isocyanate groups so as to effectively carry out the polymerization process.

One advantageous result of such preferential use of thiol crosslinkers is the minimization of reactions with the biologics being encapsulated or immobilized at locations on the molecule where attachment to the matrix is undesirable. Control of the pH of the polymerization reaction, which places a restraint upon the nucleophilic reactivity of the amines but not the thiol groups, avoids creation of extensive links to proteins within the matrix. Proteins are of course composed of a variety of amino acids, some of which contain side chain primary amines that are potentially reactive during the overall polymerization process. However, linking to such amine functionalities may well hinder the natural movement and conformation of the proteins, and in the case of living cells, it will likely alter the pattern and responsiveness of extracellular and plasma membrane proteins. The present method avoids or substantially limits occurrence of such links and the negative aspects thereof.

For example, the pKa value for the side chain primary amine of the amino acid lysine is quite basic, approximately 10.5, and that for arginine is even more basic, i.e. over 12. If the pH of the polymerization mixture is maintained approximately neutral, then the proportion of free amine suitable for participating in a nucleophilic addition, such as that shown in FIG. 1, is less than $\frac{1}{1000}^{th}$ of the total primary amine population represented by lysine side chains. In contrast, thiol groups remain nucleophilic and very reactive at neutral pH values. Although cysteine residues in proteins contain a thiol side chain, the frequency of cysteines within proteins is generally more than 3-fold lower than that of lysine, and when present, cysteines are frequently oxidized so as to form intramolecular cystine linkages in native proteins, thereby further lowering the number of available sulfhydryl groups. The overall result is a very substantial reduction in the number of multiple, potentially denaturing links between embedded proteins or cells and the polymer matrix; thus, such thiol-mediated crosslinking of hydrogel prepolymers provides improved formulations for encapsulating sensitive biological molecules and living cells.

In addition, this encapsulation method, which depends upon thiol reactions, also provides a very effective way of anchoring small organic molecules, for example organic molecules having a molecular weight between 100 and 2000 and particularly those having a molecular weight not greater than about 500, in a manner so that they fully retain their effectiveness in the hydrogel. These small molecules are derivatized to place a thiol group at a location in the molecule where it will not interfere with the secondary or tertiary configuration of the small molecule, for example, at one end of a generally linear molecule. Although the small molecule might be of such a size that it would not necessarily be retained in an encapsulating matrix of this type, the presence of the thiol group will result in a linking to an isocyanate group on the polymer and thus anchor the small organic molecule within or upon the gel in a manner such that it can assume its normal active configuration. In this manner, the encapsulation method can be used to create what might be termed chemical chips, as well as protein chips, cellular chips and the like.

Isocyanate-functional prepolymers are often prepared from relatively high molecular weight polyoxyalkylene diols or polyols that are reacted with difunctional or polyfunctional isocyanate compounds. Preferred prepolymers are ones made from polyoxyalkylene diols or polyols that comprise homopolymers of ethylene oxide units or block or random copolymers containing mixtures of ethylene oxide units and propylene oxide or butylene oxide units. In the case of such block or random copolymers, at least 75% of the units are preferably ethylene oxide units. Such polyoxyalkylene diol or polyol molecular weight is preferably from 2,000 to 30,000 and more preferably from 5,000 to 30,000. Suitable prepolymers may be prepared by reacting selected polyoxyalkylene diols or polyols with polyisocyanate, at an isocyanate-to-hydroxyl ratio of about 1.2 to about 2.2, so that essentially all of the hydroxyl groups are capped with polyisocyanate. Aliphatic, rather than aromatic isocyanates, are preferred as they provide more easily controlled polymerization. Generally, polyethylene glycol (PEG), polypropylene glycol (PPG) or copolymers thereof are preferred. The isocyanate-functional prepolymers being used preferably contain active isocyanates in an amount of about 0.1 meq/g to about 1 meq/g, and more preferably about 0.2 meq/g to about 0.8 meq/g. Should relatively low molecular weight prepolymers, e.g. less than 2,000, be used, they preferably contain a relatively high isocyanate content (about 1 meq/g or even higher). However, the polymerization rate of such smaller prepolymers may require more precise control to avoid too rapid polymerization, and thus would be less preferred for fabricating microarrays and the like. Moreover, prepolymers with a fairly high isocyanate content may have a relatively high content of free amines after polymerization, and the positive charges on such amine functionalities, at neutral pH, may increase non-specific binding of negatively charged biomolecules with the potential of resulting in higher levels of undesirable background signals. Thus, higher molecular weight prepolymers which contain a relatively low isocyanate content are preferred.

In order to enhance the diffusability of large biological molecules, it may be desirable to use low ratios of prepolymer (3–5%) relative to the total volume of the ultimate formulation. Such relatively low percentages aid in producing hydrogel compositions having the desired porosity for use in assays, bioreactors and the like. As mentioned above, the viability of entrapped biological molecules is enhanced through minimization of the involvement of amine groups by employing crosslinkers with thiol functions and maintaining a physiological pH of about 7.0, where a large percent of amines (pKa=~10) will be present as protonated species which do not react with the isocyanate functionalities. Although such an arrangement in some instances could potentially result in incomplete curing of the prepolymer, the nucleophilic activity of thiols towards isocyanates is unaffected at such pH so curing can be completed, and the overall result is one of a significant advancement in formulating PEG and/or PPG-based hydrogels for encapsulating biomaterials.

Short-chain dithiol crosslinkers, such as 1,4-dithiothreitol (mw=154), produce a fairly high speed polymerization that needs to be slowed and carefully controlled to avoid precipitation. Longer dithiol crosslinkers provide formulations for hydrogel polymerization that are more easily controlled. Crosslinkers having a back-bone of PEG and/or PPG units are one class of dithiols that provide biocompatibility and structural advantages, and such crosslinkers of molecular weight between about 500 and 10,000 are preferred, with those between about 2,000 and 6,000 being more preferred and those between about 3,000 and 4,000 being most preferred. For example, PEG-(thiol)$_2$ (Shearwater Polymers, Inc.) having a mw=3,400 and thiol groups at the ends of the chains, may be used with Hypol PreMa G-50 (Hampshire Chemical Corp., which has an aliphatic isocyanate content of ~0.35 meq/g), and by varying the ratio between two such starting materials, it was found that the speed of polymerization can generally be effectively controlled at pH 7.0. The molar ratio of dithiol crosslinker to isocyanate (from the prepolymer) is preferably not higher than about 0.3 dithiol per isocyanate, and more preferably not higher than about 0.2 dithiol per isocyanate.

Formulations having a ratio significantly lower than 0.1 dithiol per isocyanate, e.g. 0.05 or below, might not polymerize promptly and/or completely at pH 7.0 without the inclusion of an auxiliary crosslinker. Thus, formulations having a ratio slightly less than about 0.1 dithiol per isocyanate are preferably supplied with an auxiliary bidentate crosslinker having two different isocyanate-reactive functional groups, one of which is preferably thiol, e.g. cysteine which has a side chain thiol group and a less reactive primary α-amine group which is of course more nucleophilic than the α-carboxyl under these conditions. Other bidentate crosslinkers that might be used include 2-mercaptoethanol, 2-aminoethanethiol, homocysteine, 2-mercaptopropanol and other short chain compounds having a thiol group and another nucleophilic group. Morever, even when an adequate amount of the dithiol crosslinker is provided, it has been found that the provision of an auxiliary bidentate crosslinker can be advantageous in controlling the polymerization reaction in obtaining completion within desirable time limits and in obtaining hydrogel compositions that are stable, have a high water content and excellent structural strength. Accordingly, the employment of the combination of a dithiol crosslinker of relatively high molecular weight, e.g. about 2,000 to 6,000 mw, and a bidentate crosslinker of much lower molecular weight, preferably below about 300 mw, is preferred. It was found that this addition of a moderating bidentate crosslinker having two different reactive groups (e.g. cysteine) provides a novel and powerful means by which polymerization can be effectively controlled, and such is diagrammatically illustrated in FIG. 2, which also indicates that crosslinking in this manner eliminates a large amount of $CO_2$ that would otherwise be created in normal crosslinking. When such an auxiliary crosslinker is used, it is generally used in a molar amount from about 1 to 3 times the molar amount of the dithiol, and preferably from about 1.5 to about 2.5 times the moles of the dithiol crosslinker, in which amount it has been found to moderate the polymerization reaction and result in satisfactory curing.

The inherent reactivity of prepolymers of this general type allows the use of chemically functional surfaces to also achieve covalent attachment of the polymer to a substrate during polymerization. Such surfaces may be provided upon substrates which will facilitate the handling and instrumented examination of the polymerized hydrogel and encapsulated biological matter; for example, fabrication of a microarray containing different bioactive material encapsulated into individual spots or regions of polymerized hydrogel placed in a known pattern on such a substrate.

Neutral pH is preferably maintained throughout the polymerization process by the use of 50 mM phosphate buffer supplemented with NaCl, typically 10 mM to 80 mM; osmotic pressure is preferably maintained at physiological levels, approximately 300 milliosmoles. It is found that such formulations can be made without using organic solvents by mixing isocyanate-derivatized prepolymers rapidly in phosphate buffer/NaCl and then rapidly adding a premixed solution of cells or proteins and dithiol crosslinker in phosphate buffer/NaCl. The polymerization process will then generally occur within 20 to 60 minutes, typically less than 30 minutes, during which time the cells or proteins remain in a hydrated and an osmotically balanced state at physiological pH. Preferably, pH and osmolality are maintained between 6.9 to 7.6 and between 250 to 400 mOsm/kg, respectively. Once cured, polymer sites containing the encapsulated biologics are easily washed, and manipulated.

Optical examination of these thiol-crosslinked hydrogels reveals optical clarity with no background fluorescence attributable to the gel formulation and generally similar optical properties to hydrogel formulations described in the '683 patent. However, in the '683 processes, it was often very important to carefully control the rate of $CO_2$ evolution to avoid some opacity. The present process which uses dithiol crosslinkers in combination with bidentate modifiers inherently minimizes $CO_2$ evolution, as mentioned before with respect to FIG. 2, and can produce an optically transparent hydrogel with essentially no difficulty.

To show that these polyurethane hydrogels are suitable for encapsulating a wide range of biologics, encapsulation of living eukaryotic cells was first examined. One criteria for the success of encapsulation of living cells is an assessment of continued cell viability, and typically, trypan blue exclusion is a technique frequently favored by biologists to easily determine cell viability. However, because the hydrogel absorbs a significant amount of the trypan blue dye, determination of cell color and intensity of the intracellular dye using this method was unreliable. As an alternative, AlamarBlue™ (Trek Diagnostic Systems, Inc.) was used. AlamarBlue is a dye that becomes fluorescent upon reduction by metabolic processes. Goat lymphocytes, having been determined by trypan blue exclusion to have both viable and dead cells present within the cell mixture, were chosen, and the prepolymer and cell suspension/dithiol crosslinker/bidentate crosslinker were mixed. The lymphocytes became encapsulated within the thiol-crosslinked hydrogel when droplets of the mixture were deposited as spots (approximately 300–1,000 microns in diameter, with a height equal to or greater than 20 microns) upon glass slides and then cured in a high humidity chamber at room temperature; mixing and curing took just less than 20 minutes. Preferably, the relative humidity (RH) is at least about 90% and more preferably is about 95% or higher. With the spots firmly attached to the glass slide, the slide was incubated for three hours at 37° with RPM 1640 media followed by incubation for 1.5 hours with AlamarBlue™ dye that had been mixed one part to twenty with RPM1640 media. After leaving the slide for 30 minutes in the dark, visualization of the spots using an epifluorescence microscope revealed brightly stained individual cells against a moderately fluorescent hydrogel background. Visible light revealed cells within the gel which were not brightly stained, which were presumably the aforementioned dead cells already present within the cell suspension. Hydrogel-only spots treated in an analogous fashion had no visible fluorescence. Therefore, AlamarBlue™ is felt to be a useful tool for accessing cell viability within these polyurethane-PEG hydrogels, and the hydrogel itself and the polymerization process were shown to be biocompatible by the maintenance of viable cells.

Encapsulation of proteins was also examined, formulating the gel essentially as just described. Protein encapsulation was demonstrated by the sequestration/encapsulation of anti-transferrin antibody within the gel matrix during polymerization. Verification of the antibody's functionality was demonstrated by the specific binding of fluorescent dye-labeled transferrin to those sites containing the anti-transferrin antibody and not at other sites containing different antibodies or no antibodies.

As additional embodiments, encapsulated living cells and/or proteins within such a thiol-crosslinked hydrogel might be deposited as spots or regions upon support surfaces, such as glass slides, or within microwells or microchambers, such as would be present in standard 96 well, 384 well or 1536 well microtiter plates. Distinct advantages are present with both approaches. In depositing a number of discrete spots upon a single surface, each spot might contain a different entity, allowing a single incubation followed by the supply of wash solutions to contact all spots simultaneously. The use of individual microchambers would allow robotic handling of the plates and permit the use of low volumes of individual test solutions at each well. Combinations of these two approaches may also be used whereby individual chambers, arranged in a standard 96 well array or similar format, are each supplied with one or more hydrogel spots containing different entities.

Devices employing such arrays might be employed as combinatorial chemical or drug screening devices, antibody arrays, peptide arrays, cell arrays, enzymatic activity arrays, or DNA or other polynucleotide arrays that will be selective for binding to related proteins or other biomolecules. In addition, encapsulated cells or biomolecules coated onto the walls of microcapillary tubes will function as flow-through devices having single or multiple channels, which might be employed as screening devices or as biosensors on systems, such as in liquid chromatography or in "lab-on-a-chip" devices. Signal readout from such devices might be via binding of fluorescent proteins or of antigens, to be measured by subsequent antibody-based detection methods (possibly employing additional arrays), or via reaction with endogenous biopathways which will result in the formation of a detectable species, e.g. enzymatic conversion of a substrate to a fluorescent dye molecule, or change in the electrical properties, e.g. conductivity, of the cell and/or surrounding matrix resulting from exposure to the specific agent. In particular, the addition of either a redox agent to the gel or the addition of an electrically conductive polymer may enable signal detection by electrical, non-photonic, means.

The working examples which follow include the best mode presently known for providing formulations and encapsulation methods embodying particular features of the invention; however, they should be understood not to constitute limitations upon the scope of the invention which is of course defined by the claims that are set forth hereinafter.

EXAMPLE 1

Solution A was prepared by mixing 0.075 g of Hypol PreMa G-50 (Hampshire Chemical Corp.) and 1.5 mL of 50 mM aqueous phosphate buffer, at pH 7.0 with 80 mM sodium chloride. Solution B was prepared by dissolving 30 mg of PEG-(thiol)$_2$ (mw=3,400) and 2 mg of free base cysteine (Sigma Chemical Co.) (mw=121) in 1 mL of 50 mM phosphate buffer, at pH 7.0 with 60 mM sodium chloride. Solution C was prepared by mixing 100 μL of Solution B with 10 μL of goat lymphocytes in Dulbecco's phosphate-buffered saline. Finally, 200 μL of Solution A was mixed with 50 μL of Solution C, and the resulting solution was microspotted onto amine-treated glass (Silanated Slides, Cell Associates, Inc.) with the use of 5 microliter glass microcapillary tubes. The hydrogel spots were polymerized carefully in a humidity box, at about 95% RH, to avoid dehydration. This formulation polymerized within 5–10 minutes. After polymerization, the hydrogel spots were physically stable and strongly attached to the glass slide; they were immediately treated with Dulbecco's modified phosphate-buffered saline solution and incubated at either room temperature or at 37° for about 3 hours in RPM1640 cell media. The viability of lymphocytes was examined by means of the AlamarBlue staining method described previously. They were incubated for 1.5 hours with RPM1640 media plus the dye and then examined with a light microscope; viable, encapsulated cells were observed.

EXAMPLE 2

Solution A was prepared by mixing 0.1 g of Hypol PreMa G-50 (Hampshire Chemical Corp.) and 1 mL of 50 mM phosphate buffer, at pH 7.0 with 80 mM sodium chloride. Solution B was prepared by the same procedure as in Example 1. Solution C was prepared by mixing 40 μL of Solution B with 70 μL of goat lymphocytes in Dulbecco's phosphate-buffered saline. Finally, 100 μL of Solution A was mixed with 100 μL of Solution C, and the resulting solution was microspotted using the same procedure as in Example 1. The formulation polymerized in 5 minutes, and the hydrogel spots were treated with Dulbecco's modified phosphate-buffered saline solution and incubated at 37° C. for 1 day to 3 days in RPM1640 cell media. The viability of lymphocytes was examined with a light microscope using AlamarBlue which demonstrated viable encapsulated cells.

EXAMPLE 3

Solution A was prepared by mixing 0.1 g of Hypol PreMa G-50 (Hampshire Chemical Corp.) and 1 mL of 50 mM phosphate buffer, at pH 7.0 with 80 mM sodium chloride. Solution B was prepared by the same procedure as in Example 1. Solution C was prepared by mixing 40 μL of Solution B with 70 μL of E. coli in Dulbecco's phosphate-buffered saline. Finally, 100 μL of Solution A was mixed with 100 μL of Solution C, and the resulting solution was placed into a disposable culture tube. The formulation polymerized in 5 minutes, and the hydrogel was treated with Dulbecco's modified phosphate-buffered saline solution and incubated at 37° C. for 1 day in RPM1640 cell media. Viability and growth of E. coli were confirmed by observing turbidity in the hydrogel after 1 day.

EXAMPLE 4

Solution A was prepared by mixing 0.1 g of Hypol PreMa G-50 (Hampshire Chemical Corp.) and 1 mL of 50 mM phosphate buffer, at pH 7.0 with 80 mM sodium chloride. Solution B was prepared by dissolving 30 mg of PEG-(thiol)$_2$ (mw=3,400) and 2 mg of free base cysteine in 1 mL of 50 mM phosphate buffer, at pH 7.0 with 60 mM sodium chloride. 25 μL of Solution A, 10 μL of Solution B, 5 μL of 50% trehalose in DI water and 10 μL of anti-transferrin antibody (goat anti-human transferrin, 5 mg/ml, protein-G purified)(Calbiochem) were mixed, and the resulting solution was microspotted onto an amine-treated glass slide so as to form spots 300 μm to 1,000 μm in diameter and at least 20 μm in height. Other similar spots were created without the addition of the anti-transferrin antibody. The hydrogel spots were carefully polymerized in a humidity box at room temperature and 95% RH, and after polymerization, the hydrogel spots were found to be physically stable and well attached to the glass slide. The slide was treated with a PBS buffer containing 1% Bovine Serum Albumin (Sigma Chemical Co.) and 0.1% Triton X-100 (Boehringer Mannheim) for 1 hour at room temperature. Anti-transferrin in the hydrogel was interacted with Cy3-labeled transferrin (1 µg/ml in 1% bovine serum albumin, 0.1% triton X-100 in phosphate buffered saline) for 1 hour and then visualized; it demonstrated that there was specific binding of fluorescent dye-labeled transferrin at sites containing the anti-transferrin antibody and not at other sites containing different antibodies or no antibodies.

EXAMPLE 5

Solution A was prepared by mixing 0.1 g of Hypol PreMa G-50 (Hampshire Chemical Corp.) and 1 mL of 50 mM phosphate buffer at pH 7.0. Solution B without salts was prepared by the same procedure as in Example 1. Solution C was prepared by mixing 40 µL of Solution B with 70 µL of 234 µm L-alpha-cysteine-N-[8-(1,2,3,4-tetrahydro-acridin-9-ylamino)-octyl]-amide (mw=428.26), an acetylcholine esterase inhibitor, in 50 mM phosphate buffer at pH 7.0. Finally, 100 µL of Solution A was mixed with 100 µL of Solution C, and the resulting solution was microspotted using the same procedure as in Example 1. The formulation polymerized in 5 minutes, and the hydrogel microspots were treated with cy-3 labeled acetylcholine esterase. This testing confirmed presence and functionality of acetylcholine esterase inhibitor in the hydrogel.

Although the invention has been described with regard to certain preferred embodiments, it should be understood that changes and modifications as would be obvious to those having ordinary skill in this art may be made without deviating from the scope of the invention which is set forth in the claims appended hereto. The inclusion of additional polymers or modifications to the above-described polymer might permit either cell proliferation or increased viability of select cell types within the matrix. For example, peptide linkages within such a polymer may be specifically crafted to dissolve upon exposure to extracellular matrix proteases generated by the encapsulated cell, thereby dissolving the polymeric matrix as needed to permit cell expansion and growth. Alternatively, other polymers or agents, such as collagen, might be added to such a polymeric blend to aid cell viability by use of specific adhesion factors and/or binding methods between encapsulated cells and surrounding support. In contrast to spotting the hydrogel compositions onto a solid surface, hydrogel microbeads may be formed which encapsulate biologics. As one example, after mixing the prepolymer with the crosslinker and biologics, the polymer/cell (or protein) mix is added to a non-miscible liquid, such as an oil, while curing is occurring to cause microbeads of various dimensions to be formed. Separation from the oil or other suspending liquid yields a slurry of beads suitable for use in bioreactors, assay devices, artificial organs, biosensors or the like. Moreover, multiple layers of encapsulated cells, proteins or other bioactive molecules might be used to construct complex materials having unique overall properties. Alternatively, dyes or other agents might be added to the encapsulating polymer to facilitate subsequent identification of the encapsulated cell type if heterogeneous mixtures of cells are to be employed. Such a cell identification mechanism, combined with a chromaphore-based or fluorescent-based response from specific cells in response to added agents, e.g. expression of green fluorescent protein in response to specific cell signaling pathway activation by a ligand or drug, permits the screening of large populations of heterogeneous cells in a rapid and facile fashion.

The disclosures of all U.S. patents mentioned hereinbefore are incorporated herein by reference. Particular features of the invention are set forth in the claims which follow.

The invention claimed is:

1. A bioassay comprising the steps of:
   (a) providing a microarray which comprises a substrate having a plurality of discrete spots of a stabilized hydrogel composition bound thereto which composition is the reaction product of a prepolymer of polyethylene glycol, polypropylene glycol, or a copolymer thereof having isocyanate end groups, and a thio-functional crosslinking agent, which results in thio-urethane groups wherein said stabilized hydrogel composition further includes biologics encapsulated therewithin which remain bioactive;
   (b) contacting the microarray with an analyte solution, and
   (c) detecting the interactions of the microarray with the analyte solution.

2. The bioassay of claim 1 wherein said hydrogel composition is exposed to a second analyte solution as a part of said detecting step.

3. The bioassay of claim 1 wherein said analyte solution contains a marker which binds to said biologic which is a target and wherein the step of detecting comprises detecting the marker bound to the target.

4. The bioassay of claim 3 wherein the marker is capable of fluorescence and wherein the step of detecting the bound target comprises detecting fluorescence from the marker.

5. A microarray which comprises:
   a substrate, and
   a plurality of discrete spots of a hydrogel biologic composition attached to said substrate, which hydrogel biologic composition comprises:
   (a) the reaction product of a prepolymer of polyethylene glycol, polypropylene glycol, or a copolymer thereof having isocyanate end groups, and a thio-functional crosslinking agent, which results in thio-urethane groups and provides a stabilized hydrogel, and
   (b) a biologic which is encapsulated within said stabilized hydrogel and which remains bioactive.

6. The microarray of claim 5 wherein the thiol-functional crosslinking agent comprises a dithiol-functional crosslinker and a bidentate crosslinking agent having one thiol group and another different isocyanate-reactive group in a molar amount from about 1 to 3 times the molar amount of said dithiol crosslinker.

7. The microarray of claim 6 wherein said dithiol-functional crosslinking agent comprises a backbone of polyethylene glycol, polypropylene glycol, or a copolymer thereof and has a molecular weight between about 2,000 and about 6,000.

8. The microarray of claim 5 wherein said spots are spatially arranged to form a regular array and wherein the plurality of spots include some at known locations within said array wherein different biologics are entrapped.

9. The microarray of claim 5 wherein said biologics are living eukaryotic cells.

10. The microarray of claim 5 wherein said biologics are proteins or other organic molecules having a molecular weight between 100 and 2000 which have been derivatized to include a thiol group.

11. The microarray of claim 5 wherein said stabilized hydrogel is optically transparent.

* * * * *

UNITED STATES PATENT AND TRADEMARK OFFICE
CERTIFICATE OF CORRECTION

| | |
|---|---|
| PATENT NO. | : 7,172,866 B2 |
| APPLICATION NO. | : 10/398725 |
| DATED | : February 6, 2007 |
| INVENTOR(S) | : Hahn et al. |

Page 1 of 1

It is certified that error appears in the above-identified patent and that said Letters Patent is hereby corrected as shown below:

Title Sheet, Column 1, line 8 (in the abstract), change "or" to --of--; Column 12, line 8 (in claim 1), after "thereto" insert --,--; Column 12, line 12 (in claim 1), correct the spelling of --crosslinking--; Column 12, line 38 (in claim 5), correct the spelling of --crosslinking--; Column 12, lines 43 and 44 (in claim 6), correct the spelling of --crosslinking--; Column 12, lines 43-44 and 47 (in claim 6), correct the spelling of --crosslinker--; Column 12, line 49 (in claim 7), correct the spelling of --crosslinking--.

Signed and Sealed this

Twenty-second Day of May, 2007

JON W. DUDAS
*Director of the United States Patent and Trademark Office*